United States Patent [19]

Gold

[11] 3,965,176

[45] June 22, 1976

[54] NOVEL SUBSTITUTED AMIDINES

[75] Inventor: Elijah H. Gold, West Orange, N.J.

[73] Assignee: Schering Corporation, Kenilworth, N.J.

[22] Filed: Dec. 13, 1974

[21] Appl. No.: 532,437

Related U.S. Application Data

[63] Continuation-in-part of Ser. No. 371,790, June 20, 1973, abandoned.

[52] U.S. Cl. .................... 260/564 RF; 260/239 A; 424/308; 424/311; 260/239 BF; 424/316; 424/326; 260/243 R; 260/243 B; 260/244 R; 260/247; 260/247.1 R; 260/247.1 H; 260/247.2 A; 260/247.2 B; 260/247.5 R; 260/250 B; 260/293.72; 260/293.74; 260/293.77; 260/293.79; 260/326.82; 260/326.86; 260/471 C; 260/476 R; 260/481 C; 260/482 C; 260/488 CD; 260/556 A; 260/562 R; 260/564 R; 424/244; 424/246; 424/250 R; 424/267; 424/274; 424/300

[51] Int. Cl.² .................................. C07C 123/00
[58] Field of Search ............... 260/564 RF, 501.14, 260/556 A, 556 B, 558 P, 562 R

[56] References Cited

UNITED STATES PATENTS 3,284,289   12/1966   Duerr et al. ................. 260/564 RF

*Primary Examiner*—Gerald A. Schwartz
*Attorney, Agent, or Firm*—Raymond A. McDonald; Stephen B. Coan

[57] ABSTRACT

This application relates to substituted amidines, to methods for their preparation and to methods for their use as anti-androgenic agents.

12 Claims, No Drawings

NOVEL SUBSTITUTED AMIDINES

This application is a continuation-in-part of my copending application Ser. No. 371,790, filed June 20, 1973 now abandoned.

This invention relates to valuable therapeutically active chemical compounds belonging to the general class of substituted amidines and to the processes for making such compounds as well as to the processes for using them as therapeutically effective anti-androgenic agents.

The chemical compounds of this invention are more specifically described as substituted amidines of the structural formula:

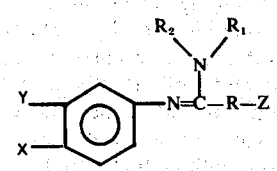

I wherein $R_1$ represents hydrogen, lower alkyl, lower cycloalkyl, hydroxy, lower alkoxy, lower cycloalkoxy, unsubstituted phenyl or phenyl substituted by nitro, trifluoromethyl or halogen, $R_2$ represents hydrogen, lower alkyl or lower cycloalkyl, or $R_1$ and $R_2$ together represent an alkylene radical having 3 to 7 carbon atoms or the radical $-CH_2-CH_2-Q-CH_2-CH_2-$ with Q being selected from $-O-$, $-S-$, $>NH$ and $>N$-lower alkyl;

X is a member of the group consisting of nitro, trifluoromethyl, chloro, bromo and iodo, Y is a member of the group consisting of hydrogen, halogen, nitro, amino, lower alkylamino, lower dialkylamino, lower alkyl, lower alkoxy, lower alkanoyl, polyfluorolower alkoxy, polyfluorolower alkyl, polyfluorolower alkylthio

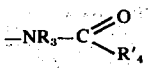

and $-NR_3SO_2R_4$ with $R_3$ being hydrogen or lower alkyl, $R_4$ being lower alkyl, aralkyl or aryl and $R'_4$ is lower alkoxy, aralkoxy, aryloxy, lower alkyl, aralkyl and aryl;

R is a divalent radical derived from an alkane or alkene either of which contains at least one secondary or tertiary carbon atom with the proviso that any double bond in said divalent radical derived from an alkene is not conjugated with the amidine double bond;

Z is a member of the group consisting of hydrogen, hydroxy, lower alkoxy, lower arylalkoxy, lower alkanoyloxy, lower arylalkanoyloxy, carbamoyloxy, thiocarbamoyloxy, mono- and di-lower alkyl carbamoyloxy and thiocarbamoyloxy, and the pharmaceutically acceptable acid addition salts thereof.

Those amidines of the formula I wherein one or both of $R_1$ and $R_2$ represent hydrogen may be subject to formation of a tautomeric equilibrium, the other tautomeric form being represented by the structural formula:

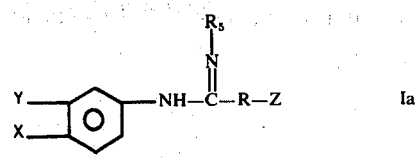

wherein X, Y, Z and R are as defined above and $R_5$ is selected from the group consisting of hydrogen, lower alkyl, lower cycloalkyl, hydroxy, lower alkoxy, lower cycloalkoxy, unsubstituted phenyl or phenyl substituted by nitro, trifluoromethyl or halogen. The amidines of the formula Ia are considered to be embraced by formula I defined above, i.e., in this specification and in the claims both tautomeric forms of the amidines are defined by means of structural formula I.

The N-lower alkyl analogues of the compounds of formula Ia are also part of this invention and are more specifically described as amidines of the structural formula:

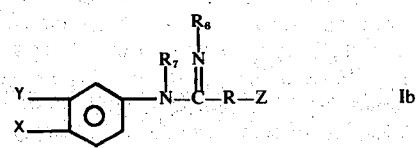

wherein $R_6$ represents hydrogen, lower alkyl, lower cycloalkyl, hydroxy, lower alkoxy, lower cycloalkoxy, unsubstituted phenyl or phenyl substituted by nitro, trifluoromethyl or halogen, $R_7$ represents lower alkyl, X is a member of the group consisting of nitro, trifluoromethyl, chloro, bromo and iodo, Y is a member of the group consisting of hydrogen, halogen, nitro, amino, lower alkylamino, lower dialkylamino, lower alkyl, lower alkoxy, lower alkanoyl, polyfluorolower alkoxy, polyfluorolower alkyl, polyfluorolower alkylthio,

and $-NR_3SO_2R_4$ with $R_3$ being hydrogen or lower alkyl and $R_4$ being lower alkyl, aralkyl or aryl;

R is a divalent radical derived from an alkane or alkene either of which contains at least one secondary or tertiary carbon atom with the proviso that any double bond in said divalent radical derived from an alkene is not conjugated with the amidine double bond;

Z is a member of the group consisting of hydrogen, hydroxy, lower alkoxy, lower arylalkoxy, lower alkanoyloxy lower arylalkanoyloxy, and di-lower alkyl carbamoyloxy;

and the pharmaceutically acceptable acid addition salts thereof.

As used herein, the term lower when used to modify such terms as alkyl, cycloalkyl, alkoxy, cycloalkoxy, alkanoyl, alkanoyloxy is meant to include those radicals having up to and including six carbon atoms. In such instances it is preferred that such radicals (except cycloalkyl and cycloalkoxy) contain less than four carbon atoms. The term polyfluoro includes those groups wherein at least two hydrogen atoms have been replaced by fluorine, and include partially fluorinated (e.g., difluoromethyl) and perfluoro (e.g., trifluoromethyl) radicals.

The term "alkylene radical having 3 to 7 carbon atoms" is meant to include those radicals having the free valences at the terminal carbon atoms of the hydrocarbon chain (e.g., butylene, pentylene).

The term "divalent radical derived from an alkane or alkene either of which contains at least one secondary or tertiary carbon atom" as used to define R embraces preferably any group of this kind having up to and including eight carbon atoms. Although substituent Z may be attached to any of the carbon atoms of the moiety R, it is preferred that such Z substituent be attached to that carbon atom directly attached to the amidine carbon atom.

The term "phenyl substituted by nitro, trifluoromethyl or halogen" is meant to include mono-or disubstituted phenyl radicals whereby in case of disubstitution the substituents need not be the same.

Exemplary of pharmaceutically acceptable acid addition salts of compounds of the formulae I and Ib are those formed with maleic, fumaric, succinic, tartaric, citric, malic, cinnamic, sulfonic, hydrochloric, hydrobromic, sulfuric, phosphoric and nitric acids. The acid addition salts may be prepared in the conventional manner, by treating a solution or suspension of the free base in an organic solvent with the desired acid, and then recovering the salt which forms by crystallization techniques.

In the preparation of the substituted amidines of formula I, a variety of methods is available, most of them depending upon the type substituent one desires the final compound to possess. A convenient method to prepare those compounds of formula I wherein Z does not represent free hydroxy and Y is not amino or lower alkylamino, comprises condensing an appropriately X,Y-substituted imidohalide (preferably chloride or bromide) with an amine containing the desired substitutents $R_1$ and $R_2$ or a reactive derivative of said amine such as a salt. The reaction may be depicted by the following structural representation:

Reaction Sequence I:

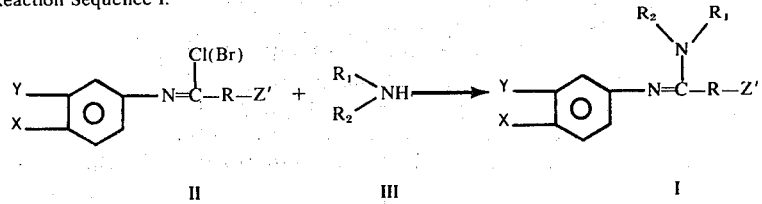

wherein X, Y, R, $R_1$ and $R_2$ are as previously defined and Z' is hydrogen, lower alkoxy, lower arylalkoxy or acyloxy, including lower alkanoyloxy, lower arylalkanoyloxy and di-lower alkyl carbamoyloy. The condensation is effected by mixing the reactants in an inert organic solvent with or without an acid acceptor. Suitable solvents include ethers, alcohols, benzene, and triethylamine. The reaction may be effected at room termperature although elevated temperatures up to the reflux temperature of the reaction mixture may also be employed. The condensation proceeds rapidly and at the completion thereof the mixture is washed, basified, if necessary, dried and thereafter the desired product is preferably isolated by precipitation as an acid addition salt and filtration thereof. The product may be further purified by usual techniques, such as by recrystallization.

The chloro or bromo imidate-starting materials (II) may readily be obtained by reacting corresponding substituted anilides (III) with equivalent quantities of halogenating agents including $PCl_5$, $PBr_5$, $POCl_3$, $POBr_3$, $COCl_2$, $SOCl_2$. This reaction takes place in a nonreactive solvent such as toluene, benzene and the like, taking precautions that the reaction is under anhydrous conditions to prevent hydrolysis of the halo imidate. The foregoing reaction is schematically depicted as follows:

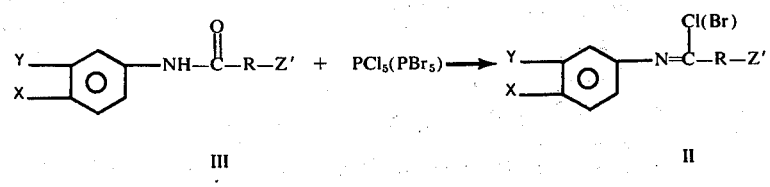

wherein X, Y, R and Z' are as previously defined.

The substituted anilides (III) may be prepared by the condensation of an appropriate X, Y-substituted aniline with an acyl halide, the condensation being effected by heating a mixture of at least equimolar quantities of the reactants in the presence of an acid acceptor. Preferably the heating of the reactants takes place in a solvent at elevated temperatures up to reflux temperature of the reaction mixture.

Another convenient method to prepare those amidines of formula I wherein Z does not represent free hydroxy is the condensation of an X,Y-substituted aniline or a reactive derivative thereof with an appropriately substituted imidate, or a salt thereof, according to the following structural representations:

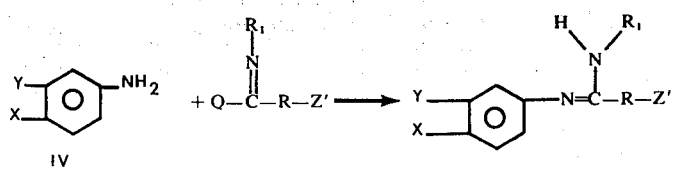

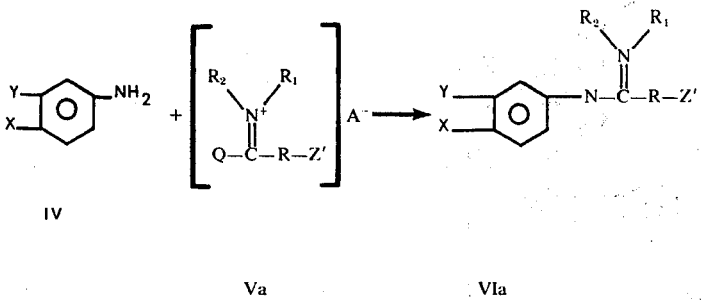

wherein X, Y, R, R$_1$ and R$_2$ are as previously defined, Q represents a group capable of being eliminated under the conditions of reaction applied. A represents an anion and Z' represents hydrogen, lower alkoxy, lower arylalkoxy or acyloxy including lower alkanoyloxy, di-lower alkyl carbamoyloxy and aryalkanoyloxy. Q may represent any strong leaving group such as halogen, alkoxy and thioalkoxy. A may represent any anion including BE$_4^-$, Cl$^-$, Br$^-$, SbF$_6^-$. The reaction is carried out in an inert organic solvent including ethers, alcohols and benzene. The temperature is not critical and the reaction is conveniently effected at room temperature with or without an added acid acceptor. After the condensation is completed the mixture is washed, basified, if necessary, dried and the desired product is preferably isolated by precipitation as an acid addition salt and filtration thereof.

The starting material (V, Va) may be prepared by treating a corresponding amide with a compound capable of introducing the moiety Q such as halogenating agents including PCl$_5$, POCl$_3$, COCl$_2$, SOCl$_2$, PBr$_5$, and alkylating agents including (alkyl$_3$)O$^+$BF$_4^-$. The reaction is carried out in an inert organic solvent such as methylene chloride or toluene and preferably at a temperature lower than room temperature or at room temperature. If it is desired the final compound of formula I to possess as substituent Z a free hydroxy group, a corresponding amidine possessing an esterified hydroxy group is subjected to hydrolysis according to methods known in the art. The reaction may be depticted by the following structural representation:

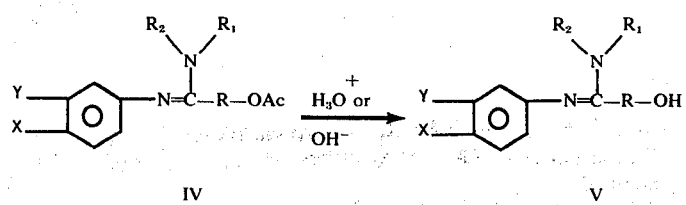

wherein X, Y, R, R$_1$ and R$_2$ are as above defined and Ac represents an acyl radical. The acyl radical may be derived from any organic acid and includes lower alknaoyl and lower arylalkanoyl radicals. The ester-starting material may be obtained by any of the herein described appropriate reactions and preferably by reacting compound IV with compound V or Va as hereinabove described.

Another convenient method for the preparation of the amidines of formula I wherein substituent Z does not represent freee hydroxy, and Y is not amino, alkylamino or dialkylamino, is the introduction of substituent X into an amidine molecule possessing all the other substituents desired. The reaction is effected according to aromatic substitution reactions known in the art, for example, the nitro group is introduced by subjecting the starting material to a mixture containing nitric acid and sulfuric acid. The reaction may be depicted by the following schematic representation:

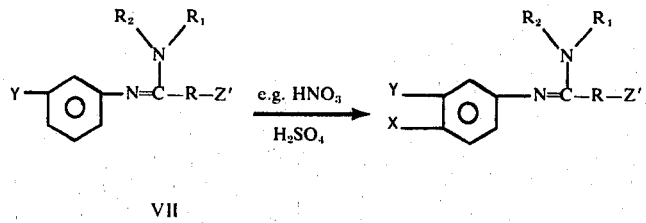

wherein X, Y, R, R$_1$, R$_2$ and Z' are as defined above. The starting material VII may be prepared according to the following reaction scheme:

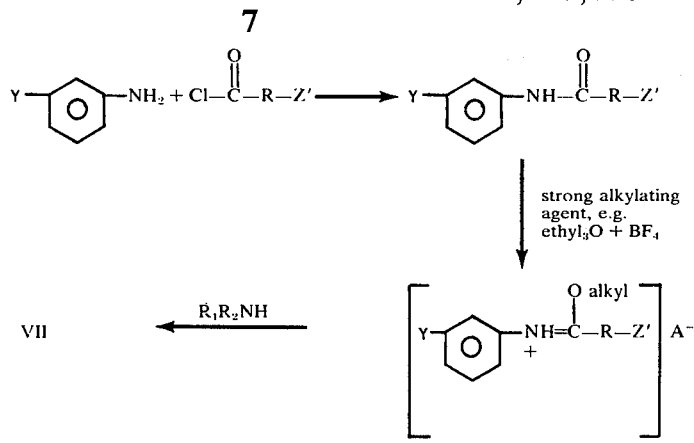

wherein Y, R, $R_1$, $R_2$, Z' and $A^-$ are as defined above.

Formation of the amide by reacting the aniline with the acid-chloride, preparation of the imidate salt and reaction thereof with the $R_1$, $R_2$ containing amine are effected under conditions described above for similar reactions.

In those instances wherein the required X, Y aniline reactants are not per se known, then such reactants may be prepared according to skills well known in the art. For example, in those instances wherein the Y-substituent is a polyfluoroloweralkyl radical (other than a perfluoro radical such as difluoromethyl or α,α-difluoroetnyl, the compound bearing such substituent may be prepared by heating m-nitrobenzaldehyde or m-nitroacetophenone with sulfur tetrafluoride under pressure to form the corresponding difluoro compound. Hydrogenation of the nitro group affords the m-substituted aniline which may be acylated as described above.

The amidines of formula I wherein Z does not represent free hydroxy may also be prepared by condensing an N-arylimidate or a salt thereof with an $R_1$, $R_2$ containing amine or a reactive derivative thereof according to the following schematic representation:

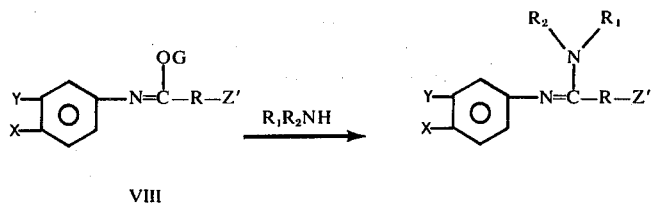

wherein X, Y, Z', R, $R_1$ and $R_2$ are as previously defined and G represents an organic moiety such as an alkyl or arylalkyl radical including methyl, ethyl or benzyl. Compounds VIII may be used as salts and typical anions of salts are $BF_4^-$, $Cl^-$, $Br^-$, $SbF_8^-$. The starting materials VIII may be obtained by reacting a compound of formula II with GOH or a salt thereof with G being as above defined.

The amidines of formula I, where Z does not represent free hydroxy, may also be prepared by condensing an amide or thioamide with an amine or a reactive derivative thereof. The amide or thioamide either contains the groups $R_1$ and $R_2$ or the X and Y substituted phenyl moiety and the amine or the reactive derivative thereof contains those structural elements of the amidine missing in the amide or thioamide.

The reaction may be depicted by the following two schematic representations:

Reaction Sequence II:
(A):

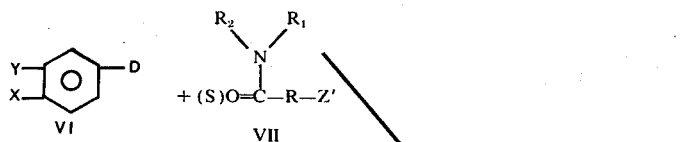

(B):

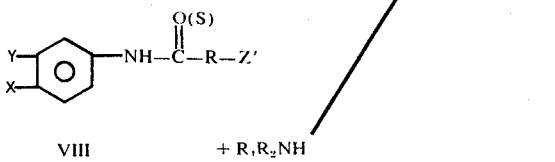

wherein X, Y, Z', R, $R_1$ and $R_2$ are as previously defined and D represents —$NH_2$, —N=C=O or —NH—CO-halogen. Both reactions (A) and (B) are effected in the presence of a condensing agent including $PCl_5$, $POCl_3$, $PCl_3$, $SOCl_2$ and $COCl_2$. In reaction (B) the $R_1$, $R_2$ containing amine may be replaced by the corresponding $R_1$ containing isocyanate or carbamic acid halide. ($R_1$ -N=C=O,

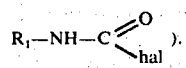

Reaction (B) can also be effected in the presence of such condensing agents as p-toluenesulfonic acid or titanium tetrachloride. In those instances wherein $R_1$ and $R_2$ represent lower alkyl, the $R_1$ and $R_2$ containing amine as used in reaction (B) can be replaced with a tetrakis (dilower alkylamino) titanium compound according to the following schematic representation:

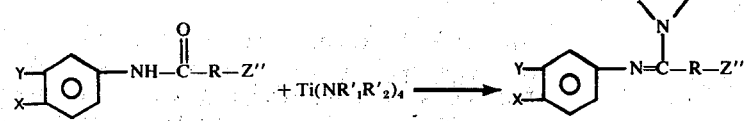

wherein X, Y, R are as previously defined, Z'' represents hydrogen, lower alkoxy or lower arylalkoxy and both $R'_1$ and $R'_2$ are lower alkyl. In case a tetrakis (dilower alkylamino) titanium compound is used, there need not be present a condensing agent and the reagents may be mixed in an unreactive solvent such as ether, benzene or tetrahydrofurane in order to obtain the desired amidine.

A further convenient method for the preparation of amidines of formula I, wherein Z does not represent free hydroxy and $R_1$ does not represent free or etherified hydroxy consists in the reaction between an X and Y substituted aniline or a salt thereof and a nitrile according to the following schematic representation:

Reaction Sequence III:

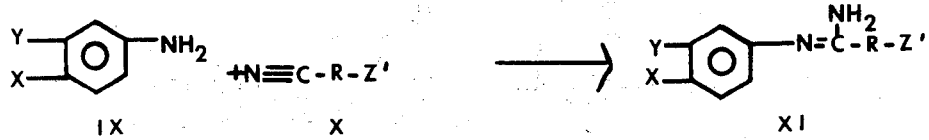

wherein X, Y, Z', and R are as previously defined. The reaction may be effected in the presence of a catalyst such as $AlCl_3$ or NaH and in an inert organic solvent. If it is desired the final compound to possess $R_1$ and $R_2$ substituents other than hydrogen, the reaction is effected in the presence of a compound capable of introducing the desired group such as a strong alkylating agent including $(alkyl)_3O^+BF_x^-$.

Another method for obtaining compounds of formula I compriese subjecting a compound of the general formula:

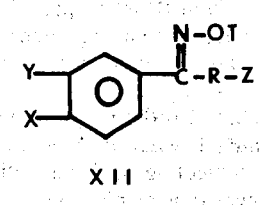

wherein X, Y, Z and R are as defined above, T is an organic moiety such as an acyl radical including —$SO_2$—alkyl, —$SO_2$—aryl and —$SO_2$—arylalkyl, to conditions allowing a Beckmann rearrangement in the presence of an amine $R_1R_2NH$, wherein $R_1$ and $R_2$ are as previously defined. The conditions of reaction are those known to the art for this kind of reaction.

A further method for the preparation of compounds of formula I wherein Z does not represent free or esterified hydroxy consists of the reaction between an appropriately substituted carbodiimide and an —R—Z'' containing magnesium halide according to the following schematic representation:

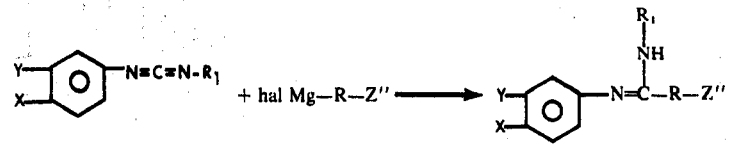

wherein X, Y, Z'', R, and R₁ are as above defined and hal represents halogen. The reaction is carried out in an inert organic solvent.

Yet another method for preparing compounds of the general formula I wherein R₁ and R₂ represent hydrogen comprises subjecting a compound of the general formula:

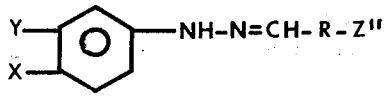

wherein X, Y, Z'' and R are as previously defined, to conditions allowing a rearrangement reaction. The reaction is carried out in the presence of a catalyst such as NaNH₂.

A suitable method for the preparation of those compounds of formula I, wherein X is chloro, bromo or iodo comprises subjecting to diazotization and to subsequent Sandmeyer-type displacement reaction, a compound of the general formula:

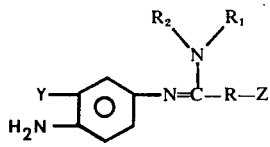

XIII wherein Z, R, R₁ and R₂ are as above defined and Y is not amino or an alkyl amino moiety.

Another method for the preparation of the compounds of the general formula I comprises eliminating a group capable of being eliminated under conditions not giving rise to structural changes of the amidine formation from a compound of the general formula:

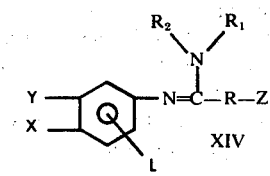

XIV wherein X, Y, Z, R, R₁ and R₂ are as above defined and L represents a grouping capable of being eliminated under the conditions of reaction applied. Substituent L may represent the —NH₂ group which is eliminated by diazotization (when Y is not an amino moiety) and reduction under standard conditions. Reduction can be effected with an alcohol, hydrophosphorous acid or formaldehyde. Substituent L may also represent Cl, Br or I if X and Y do not represent nitro or halogen and the elimination thereof may be effected by hydrogenation.

Yet another method for the preparation of the compounds of formula I, wherein Z represents hydrogen and R represents a saturated hydrocarbon moiety comprises reducing a compound of the general formula:

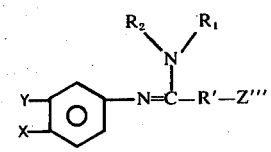

wherein X, Y, R₁ and R₂ are as defined above, Z''' is hydrogen and R' represents a divalent radical derived from an alkene having at least one secondary or tertiary carbon atom whereby the double bond in said divalent radical derived from an alkene is conjugated with the amidine double bond. A typical example for the group —R'—Z''' is isopropenyl. The reduction may be carried out with hydrogen in the presence of a suitable catalyst (Pt,Pd).

In the preparation of the substituted amidines of formula Ib, substantially the above described processes for the preparation of the compounds of formula I are applicable whereby, of course, the starting materials used are different from the starting materials used in the above described processes.

A convenient way to prepare the compounds of the general formula Ib wherein Z does not represent free hydroxy comprises condensing an X,Y,R₇ substituted aniline or a salt thereof with an appropriately substituted imidate or a salt thereof according to the following structural representations:

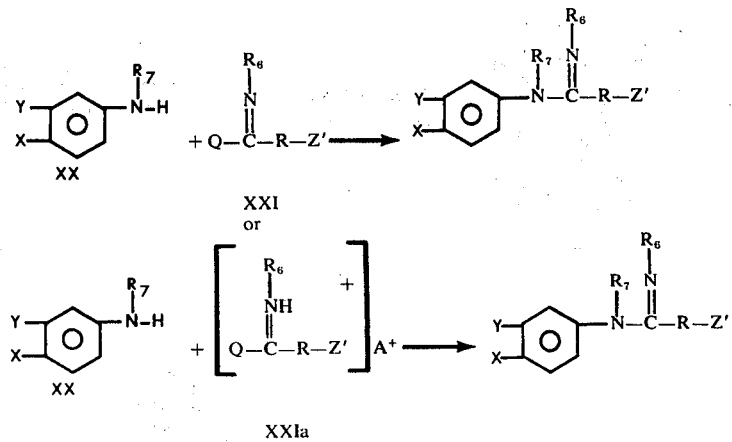

wherein X, Y, Z', R, R₆ and R₇, Q and A are as above defined. The reaction is carried out in an inert organic solvent including ethers, alcohols and benzene. Any temperature up to reflux temperature of the reaction mixture may be employed and the reaction is conveniently carried out at room temperature with or without an added acid acceptor. After the condensation is completed the mixture is washed, basified, if necessary, dried and the desired product is preferably isolated by precipitation as an acid addition salt and filtration thereof.

The imidate starting materials may be obtained by treating a corresponding amide with a compound capable of introducing the moiety Q such as halogenating wherein X, Y, R, R₆ and R₇ are above defined and Ac represents an acyl radical. The acyl radical may be derived from any organic acid and includes lower alkanoyl and lower aryl-alkanoyl radicals. The ester-starting material may be obtained by any of the herein described appropriate reactions and preferably by reacting compound (XX) with compound (XXI) or (XXIa) as hereinbefore described.

The compounds of the general formula Ib, wherein Z does not represent free hydroxy and X is not nitro, may also be prepared by reacting an appropriately substituted imidohalide with an amine or a reactive derivative thereof according to the following reaction sequence:

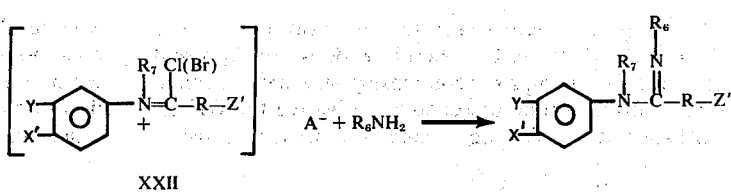

XXII agents including PCl₅, POCl₃, COCl₂, SOCl₂, PBr₅ and alkylating agents including (alkyl)₃O⁺BF₄⁻. The reaction is carried out in an inert organic solvent such as methylene chloride or toluene and preferably at a temperature lower than room temperature or at room temperature.

For example N¹-methyl-N¹-(4-nitro-3-trifluoromethyl-phenyl)-N²-methyl-isobutyramidine is prepared according to the above described reaction in the following manner: To N-methyl-isobutyramide in a solvent such as toluene is added phosphorous pentachloride at room temperature. After the reaction is completed, the resulting mixture is refluxed for 24 hours. The solvent and phosphorous oxychloride are removed and the so obtained N-methyl-isobutyrimidyl chloride together with N-methyl-4-nitro-3-trifluoromethylaniline is mixed with an inert solvent such as ethanol and the mixture is stirred for several days. The reaction mixture is basified, the solvent is removed, the residue is redissolved in a suitable solvent such ether and then washed and dried and the desired product precipitated as its acid addition salt. The amidine may be purified by recrystallization techniques known to the art.

If it is desired the final compound of formula Ib to possess as substituent Z a free hydroxy group, a corresponding amidine possessing an esterified hydroxy group is subjected to hydrolysis according to methods known to the art. The reaction may be depicted by the following structural representation:

wherein Y, Z', R, R₆ and R₇ are as defined above, x' represents trifluoromethyl, chloro, bromo or iodo and A represents an anion. The conditions of reaction applied are substantially those as described above for reaction sequence I.

Instead of using the haloimidate (XXII) an imidate (XXIII)

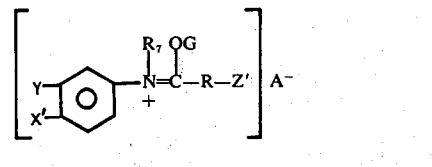

XXIII wherein X', Y, Z', R₇, A and G are as above defined, may be used in the above reaction.

Another way to obtain the compounds of the general formula Ib, wherein Z does not represent free hydroxy, comprises introducing substituent X into an amidine molecule possessing all the other substituents desired. The reaction is effected according to aromatic substitution reactions known in the art, for example, the nitro group is introduced by subjecting the starting material to a mixture containing nitric acid and sulfuric acid. The reaction may be depicted by the following sche-

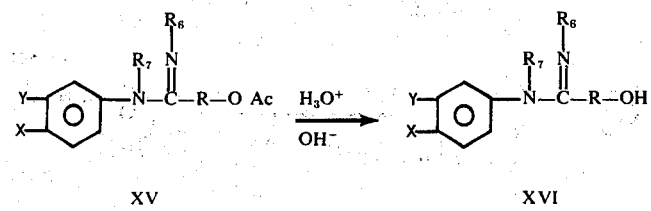

XV        XVI matic representation:

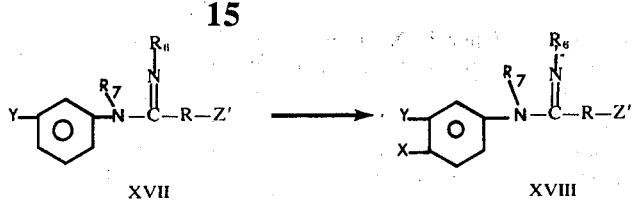

wherein X, R, $R_6$, $R_7$ and Z' are as defined above and Y is not an amino or an alkyl aminomoiety.

or a salt thereof with a nitrile according to the following schematic representation:

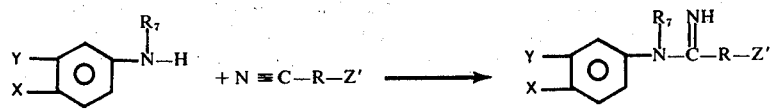

Yet another method for the preparation of those amidines of formula Ib, wherein Z does not represent free hydroxy, comprises condensing an amide or thioamide with an amine or reactive derivative thereof according to the following schematic representations:

wherein X, Y, Z and $R_7$ are as above defined. The conditions of reaction applied are substantially those as described above for reaction sequence III. In case it is desired the final compound to possess an $R_6$ substituent other than hydrogen, the reaction is effected in the (C)

(D)

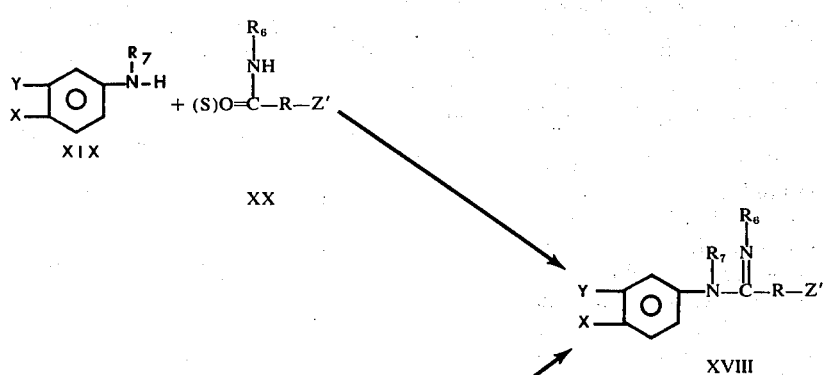

wherein X, Y, Z', R, $R_6$ and $R_7$ are as defined above.

The conditions of reaction applied are those as described for reaction sequence II above, reactions (A) and (B). The amine in reaction (C) may be replaced with its salt and the amine in reaction (D) may be replaced with its salt, the corresponding isocyanate or carbamic acid halide.

presence of a compound capable of introducing the desired group such as a strong alkylating agent including $(alkyl)_3O^+BF_4^-$.

Still a further method for the preparation of compounds of formula Ib, wherein Z does not represent free or esterified hydroxy comprises a reaction according to the following schematic representation:

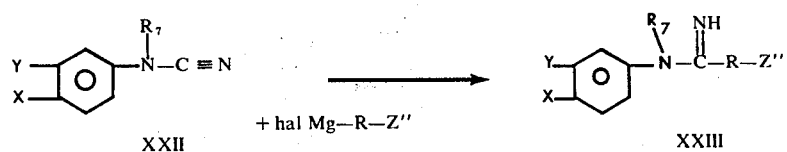

A further method for the preparation of amidines of formula Ib, wherein Z does not represent free hydroxy and $R_6$ does not represent free or etherified hydroxy comprises reacting an X, Y and $R_7$ substituted aniline wherein X, Y, Z'', R and $R_7$ are as above defined and hal represents halogen.

A suitable method for the preparation of those compounds of formula Ib, wherein X is chloro, bromo or iodo comprises subjecting a compound of the general formula:

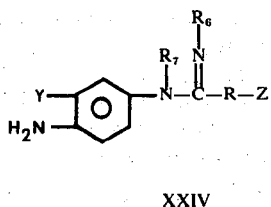

XXIV wherein Z, R, $R_6$ and $R_7$ are as above defined and Y is not amino or an alkyl amino moiety to diazotization and to subsequent Sandmeyer-type displacement reaction.

Another method for the preparation of the compounds of the general formula Ib comprises eliminating a group capable of being eliminated under conditions not giving rise to structural changes of the amidine formation from a compound of the general formula:

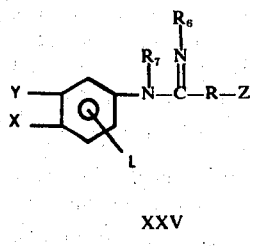

XXV wherein X, Y, Z, R, $R_6$ and $R_7$ are as above defined and L represents a grouping capable of being eliminated under the conditions of reaction applied. Substituent L may represent the —$NH_2$ group which is eliminated by diazotization and reduction under standard conditions (when Y is not amino or an alkylamino moiety). Reduction can be effected with an alcohol, hypophosphorous acid or formaldehyde. Substituent L may also represent Cl, Br or I is X and Y do not represent nitro or halogen and the elimination thereof may be effected by hydrogenation.

Yet another method for the preparation of the compounds of formula Ib, wherein Z represents hydrogen and R represents a saturated hydrocarbon moiety comprises reducing a compound of the general formula:

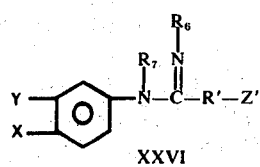

XXVI wherein X, Y, $R_6$ and $R_7$ are as defined above, $Z'''$ is hydrogen and $R'$ represents a divalent radical derived from an alkene having at least one secondary or tertiary carbon atom whereby the double bond in said divalent radical derived from an alkene is conjugated with the amidine double bond. A typical example for the group —$R'$ —$Z'''$ is isopropenyl. The reduction may be carried out with hydrogen in the presence of a suitable catalyst (Pt, Pd).

In converting one product of the general formula I or Ib into another product of the general formula I or Ib, respectively, a variety of methods is available. Compounds of formula I, wherein $R_1$ represents hydrogen or hydroxy and/or $R_2$ represents hydrogen may be alkylated by means of an alkylating agent in order to obtain compounds of formula I, wherein $R_1$ represents lower alkyl, lower cycloalkyl, lower alkoxy, or lower cycloalkoxy and/or $R_2$ represents lower alkyl or lower cycloalkyl. The alkylation is effected by subjecting the amidine compound to reaction with a compound $R_8$-$X_1$ wherein $R_8$ represents lower alkyl or lower cycloalkyl and $X_1$ is a group capable of being eliminated under the conditions of reaction applied (e.g. halogen, arylsulfonyloxy, alkylsulfonyloxy. In a similar manner compounds of the formula Ib, wherein $R_6$ represents hydrogen or hydroxy, may be converted into those compounds of formula Ib, wherein $R_6$ represents lower alkyl, lower cycloalkyl, lower alkoxy or lower cycloalkoxy.

Compounds of the formula I or Ib, wherein Y represents the free amino group may be subject to modifications in order to obtain other compounds of formula I or Ib, respectively. The free amino group may be alkylated or acylated according to methods known in the art (including alkylation via the Schiff's base) or may be converted into a halogen atom by subjecting the compound to diazotization and subsequent Sandmeyer-type displacement reaction. On the other hand, an acylated amino group may selectively be hydrolyzed in order to obtain the free amino group. The free amino group may also be obtained by reducing a corresponding nitro substituted amidine, whereby, of course, substituent X is other than nitro.

Compounds of formula I, or Ib, wherein Z represents lower alkoxy, lower arylalkoxy, lower alkanoyloxy, lower arylalkanoyloxy or di-lower alkyl carbamoyloxy may be subjected to ether cleavage or hydrolysis. In order to obtain the corresponding compounds, wherein Z represents free hydroxy. Those compounds of formula I or Ib, wherein Z represents free hydroxy may be esterified or etherified yielding compounds of formula I or Ib wherein Z represents lower alkoxy, lower arylalkoxy, lower alkanoyloxy, lower arylalkanoyloxy or di-lower alkyl carbamoyloxy.

Compounds of formula I, wherein $R_1$ and $R_2$ together represent the moiety —$CH_2$—$CH_2$—NH—$CH_2$—$CH_2$— may be alkylated in order to replace the N-hydrogen atom with lower alkyl.

Furthermore, compounds of formula I or Ib, wherein R is a divalent radical derived from an alkene which contains at least one secondary or tertiary carbon atom, whereby any double bond is not conjugated with the amidine double bond, may be subjected to hydrogenation whereby the corresponding compounds of formula I or Ib containing a divalent radical derived from an alkane are obtained.

The preparation of the compounds of formula I is illustrated by the following specific examples.

EXAMPLE 1

N',N'-Dimethyl-N²-(4-nitro-3-trifluoromethylphenyl)-isobutyramidine

To a solution of 25.2 g. (0.56 moles) of dimethylamine in 125 ml. of ethanol, add 75.0 g. (0.255 moles) of N-(4-nitro-3-trifluoromethylphenyl)isobutyrimidyl chloride in 500 ml. of ether, dropwise with cooling. Stir at room temperature for 1.5 hours, add 500 ml. of water, extract with ether, wash with saturated aqueous sodium bicarbonate solution, followed by water and dry over magnesium sulfate. Filter and precipitate the product of this example as its hydrochloride salt, by adding 120 ml. of 4.5 N ethereal hydrogen chloride, decanting the ether and triturating with ethyl acetate.

Recrystallize from methanol-ethyl acetate and obtain analytically pure product, m.p. = 205°–209° dec.

Prepare by starting with N-(3-bromo-4-nitrophenyl)-isobutyrimidyl chloride, N-(3-iodo-4-nitrophenyl)-isobutyrimidyl chloride, N-(3-chloro-4-nitrophenyl)-isobutyrimidyl chloride, N-(4-chloro-3-trifluoromethylphenyl)-isobutyrimidyl chloride, N-(4-bromo-3-trifluoromethylphenyl)-isobutyrimidyl chloride, N-(4-iodo-3-trifluoromethylphenyl)-isobutyrimidyl chloride, N-(4'-nitro-3'-trifluoromethylphenyl)-2-methoxy-isobutyrimidyl chloride or N-(4'-nitro-3'-trifluoromethylphenyl)-3-methyl-3-butenoimidyl chloride and by substantially following the procedure of this example, $N^1,N^1$-dimethyl-$N^2$-(3-bromo-4-nitrophenyl) isobutyramidine, $N^1,N^1$-dimethyl-$N^2$-(3-iodo-4-nitrophenyl)isobutyramidine, $N^1,N_1$-dimethyl-$N^2$-(3-chloro-4-nitrophenyl)-isobutyramidine, $N^1,N^1$-dimethyl-$N^2$-(4-chloro-3-trifluoromethylphenyl)isobutyramidine, $N^1,N^1$-dimethyl-$N^2$-(4-bromo-3-trifluoromethylphenyl)isobutyramidine, $N^1,N^1$-dimethyl-$N^2$-(4-iodo-3-trifluoromethylphenyl)isobutyramidine, $N^1,N^1$-dimethyl-$N^2$-(4'-nitro-3'-trifluoromethylphenyl)-2-methoxy-isobutyramidine, $N^1,N^1$-dimethyl-$N^2$-(4'-nitro-3'-trifluoromethylphenyl)-3-methyl-3-butenoamidine, respectively.

Similarly, prepare $N^1,N^1$-dimethyl-$N^2$-(4'-nitro-3'-trifluoromethylphenyl)-3-methoxy-isovaleroamidine, $N^1,N^1$-dimethyl-$N^2$-(4-nitro-3-trifluoromethylphenyl)-isovaleroamidine, $N^1,N^1$-dimethyl-$N^2$-(4'-nitro-3'-trifluoromethylphenyl)-2,3-dimethylvaleroamidine, $N^1,N^1$-dimethyl-$N^2$-(4'-nitro-3'-trifluoromethylphenyl)-2,3-dimethylbutyramidine, $N^1,N^1$-dimethyl-$N^2$-(4'-nitro-3'-trifluoromethylphenyl)-2-methylbutyramidine, $N^1,N^1$-dimethyl-$N^2$-(4'-nitro-3'-trifluoromethylphenyl)-2-ethylbutyramidine, $N^1,N^1$-dimethyl-$N^2$-(4'-nitro-3'-trifluoromethylphenyl)-2,3-dimethyl-3-butenoamidine, $N^1,N^1$-dimethyl-$N^2$-(4'-nitro-3'-trifluoromethyl-phenyl)-2,3-dimethyl-4-pentenoamidine, $N^1,N^1$-dimethyl-$N^2$-(4'-nitro-3'-trifluoromethylphenyl)-2,3-diethyl-3-butenoamidine. Similarly, by appropriately substituting dimethylamine, and by following substantially the procedure of this example, prepare $N^1$-cyclopropyl-$N^1$-methyl-$N^2$-(4-nitro-3-trifluoromethylphenyl) isobutyramidine, $N^1$-cyclohexyl-$N^2$-(4-nitro-3-trifluoromethylphenyl-)isobutyramidine, $N^1,N^1$-pentamethylene-$N^2$-(4-nitro-3-trifluoromethylphenyl)isobutyramidine, 1-(4-methyl-1-piperazyl)-N-(4'-nitro-3'-trifluoromethylphenyl)-isobutyraldimine.

EXAMPLE 2

N²-(4-Nitro-3-trifluoromethylphenyl)isobutyramidine

To a solution of 29 ml. (0.13 moles) of a 4.5N ethanolic solution of ammonia add 17.7 g. (0.060 moles) of N-(4-nitro-3-trifluoromethylphenyl) isobutyrimidyl chloride in 200 ml. of dry ether and stir for 2 hours. Add saturated sodium bicarbonate, extract with ether, dry over magnesium sulfate, filter, add 16 ml. of 4.5N ethereal hydrogen chloride to the filtrate and obtain the product of this example as its hydrochloride salt. Recrystallize from methanol-ethyl acetate and obtain analytically pure product, m.p.=238°–239°C, dec.

EXAMPLE 3

$N^1$-hydroxy-$N^2$-(4-nitro-3-trifluoromethylphenyl)isobutyramidine

Prepare a solution of hydroxylamine in methanol by adding a solution of 5.0 g. (0.072 moles) of hydroxylamine hydrochloride in 50 ml. of dry methanol to a solution of 3.6 g. (0.066 moles) sodium methoxide in 30 ml. of methanol, with stirring and cooling. To this solution, add 8.84 g. (0.030 moles) of N-(4-nitro-3-trifluoromethylphenyl)isobutyrimidyl chloride in 100 ml. of ether, with stirring and cooling. Stir two hours at room temperature, add water, extract with ether and wash well with water. Dry over magnesium sulfate, filter, add 20 ml. of 4.5 N ethereal hydrogen chloride and obtain the product of this example as its hydrochloride salt. Recrystallize from methanol ethyl acetate and obtain analytically pure product, m.p.=183°–186°C, dec.

EXAMPLE 4

$N^1$-Methyl-$N^1$-phenyl-$N^2$-(4-nitro-3-trifluoromethylphenyl)isobutyramidine To a solution of 7.3 g. (0.068 moles) of N-methylaniline and 3.45 g. (0.034 moles) of triethylamine in 50 ml. of dry ether, add 10.0 g. (0.034 moles) of N-(4-nitro-3-trifluoromethylphenyl)isobutyrimidyl chloride in 50 ml. of dry ether and stir for 1 hour. Wash with water, extract with 10% hydrochloric acid, basify the acid extract with saturated aqueous sodium bicarbonate and extract with ether. Dry over magnesium sulfate, filter and add 6 ml. of 5.4N ethereal hydrogen chloride. Allow the oil to settle and wash three times with ether by decantation. To the residue add 100 ml. of ether and 100 ml. of water and after complete dissolution of the residue, keep the ether layer, dry over magnesium sulfate, filter, remove the solvent and triturate the resulting material with cold hexane to obtain the product of this example. Recrystallize from hexane at −20°C to give analytically pure product, m.p. 52.5°–54°C.

EXAMPLE 5

$N^1$-Methyl-$N^2$-(4-nitro-3-trifluoromethylphenyl)-isobutyramidine
Method 1:

Add 8.84 g. (0.030 moles) of N-(4-nitro-3-trifluoromethylphenyl)isobutyrimidyl chloride in 100 ml. of dry ether to 220 ml. (0.066 moles) of 3.0M ethanolic solution of methylamine. Stir for 1 hour and then add water. Extract with ether, dry over magnesium sulfate, filter, remove the solvent and obtain the product of this reaction, m.p.=58°–60°C. Prepare the analytically pure hydrochloride salt, by dissolving the base in ether, adding an excess of ethereal hydrogen chloride and recrystallizing from methanol-ethyl acetate, m.p.=202°–203°C dec.

METHOD 2:

A. Ethyl-N-(3-trifluoromethylphenyl)isobutyrimidate

Add a solution of 5.0 g. (0.03 moles) of triethyloxonium fluoborate in 13 ml. of dichloromethane to a solution of 7.3 g. (0.03 moles) of 3′-trifluoromethylisobutyranilide in 60 ml. of dichloromethane and reflux for 20 hours. Remove 50 ml. of dichloromethane and add 150 ml. of dry ether to precipitate out the product of this example as its fluoborate salt, m.p.=95°–100°C.

B.

$N^1$-Methyl-$N^2$-(3-trifluoromethylphenyl)isobutyramidine

To a solution of 3.6 g. (1.16 moles) of methylamine in 30 ml. of absolute ethanol, add 20.0 g. (0.05 moles) of ethyl-N-(3-trifluoromethylphenyl)isobutyrimidate fluoborate and stir for 24 hours at room temperature. Remove the solvent, add 60 ml. of saturated aqueous sodium bicarbonate and extract with ether. Dry over magnesium sulfate, remove the ether, triturate with hexane and obtain the analytically pure product of this example, m.p.=52°–54°C.

C.

$N^1$-Methyl-$N^2$-(4-nitro-3-trifluoromethylphenyl)isobutyramidine

To a stirred mixture of 3.0 ml. of concentrated sulfuric acid and 0.14 ml. (0.0029 moles) of 90% nitric acid, cooled to 5°C, add portionwise over an eight minute period, 0.611 g. (0.0025 moles) of $N^1$-methyl-$N^2$-(3-trifluoromethylphenyl)isobutyramidine. Maintain the temperature at 5°–10°C. Stir for 1.5 hours, pour into 40 ml. of ice water, add saturated aqueous sodium bicarbonate (while cooling in an ice bath) until the mixture is basic and extract with ether. Dry over magnesium sulfate, filter, add 1 ml. of 4.5N ethereal hydrogen chloride and obtain the product of this example as its hydrochloride salt.

EXAMPLE 6

A.

$N^1$-Methyl-$N^2$-(4-bromo-3-trifluoromethylphenyl)-2-acetoxy isobutyramidine

Over a five minute period, add a solution of 17.5 g. (0.10 moles) of triethyloxonium fluoborate in 50 ml. of methylene chloride to a mixture of 15.9 g. (0.10 moles) of N-methyl-2-acetoxyisobutyramide in 200 ml. of dry methylene chloride at 0°–5°C. Allow to warm to room temperature and stir for sixteen hours. Remove the solvent in vacuo and obtain the crude product of this reaction as its fluoborate salt. Dissolve the crude fluoborate salt in 150 ml. of anhydrous ethanol, add 24.0 g. (0.10 moles) of 4-bromo-3-trifluoromethylaniline and stir for three days. Remove the solvent in vacuo and partition the residue between ether and saturated aqueous sodium bicarbonate solution. Retain the ether solution, dry it over sodium sulfate and precipitate the product of this reaction as its hydrochloride salt, by adding 0.10 moles of ethereal hydrogen chloride (25 ml. of a 4.0N solution).

EXAMPLE 7

B.

$N^1$-Methyl-$N^2$-(4-bromo-3-trifluoromethylphenyl)-2-hydroxyisobutyramidine

To a solution of 38.1 g. (0.1 moles) of $N^1$-methyl-$N^2$-(4-bromo-3-trifluoromethylphenyl)-2-acetoxy isobutyramidine in 500 ml. of ethanol, add 5.6 g. (0.1 moles) of potassium hydroxide, maintaining the reaction at room temperature. Stir at room temperature for several hours (until there is no evidence of starting ester by tlc). Remove the solvent in vacuo, partition the residue between ether and water, dry the ether extract over sodium sulfate, filter, and precipitate the product of this reaction as its hydrochloride salt, by adding 25 ml. of 4.0N ethereal hydrogen chloride.

EXAMPLE 8

$N^1,N^1$-Dimethyl-$N^2$-(4-bromo-3-trifluoromethylphenyl)-2-acetoxy isobutyramidine Over a five minute period, add a solution of 14.8 g. (0.10 moles) of trimethyloxonium fluoborate in 50 ml. of methylene chloride to a mixture of 38.1 g. (0.10 moles) $N^1$-methyl-$N^2$-(4-bromo-3-trifluoromethylphenyl)-2-acetoxyisobutyrimidate in 200 ml. of dry methylene chloride at 0°–5°C. Allow to warm to room temperature and stir for 16 hours. Remove the solvent and obtain the product of this example as its fluoborate salt. Obtain the free base by treatment with sodium bicarbonate and obtain the hydrochloride salt by dissolving the free base in ether and precipitating the salt by addition of ethereal hydrogen chloride.

EXAMPLE 9

$N^1,N^1$-Dimethyl-$N^2$-(4-bromo-3-trifluoromethylphenyl)-2-hydroxyisobutyramidine (V)

To a solution of 39.5 g. (0.1 moles) of $N^1,N^1$-dimethyl-$N^2$-(4-bromo-3-trifluoromethylphenyl)-2-acetoxyisobutyramidine in 500 ml. of ethanol, add 5.6 g. (0.1 moles) of potassium hydroxide, maintaining the reaction at room temperature. Stir for several hours (until there is no evidence of starting ester by tlc). Remove the solvent in vacuo, partition the residue between ether and water, dry the ether extract over sodium sulfate, filter and precipitate the product of this reaction as its hydrochloride salt, by adding 25 ml. of 4.0N ethereal hydrogen chloride.

Similarly, prepare $N^1$-methyl-$N^2$-(4-chloro-3-trifluoromethylphenyl)2-acetoxyisobutyramidine and the corresponding 2-hydroxyisobutyramidine, $N^1$, $N^1$-dimethyl-$N^2$-(4-chloro-3-trifluoromethylphenyl)-2-acetoxyisobutyramidine and the corresponding 2-hydroxyisobutyramidine, $N^1$-methyl-$N^2$-(3-bromo-4-nitrophenyl)-2-acetoxyisobutyramidine and the corresponding 2-hydroxyisobutyramidine, $N^1$, $N^1$-dimethyl-$N^2$-(3-bromo-4-nitrophenyl)-2-acetoxyisobutyramidine and the corresponding 2-hydroxyisobutyramidine, $N^1$, $N^1$-dimethyl-$N^2$-(4-nitro-3-trifluoromethylphenyl)-2-acetoxyisobutyramidine and the corresponding 2-hydroxyisobutyramidine, $N^1$, $N^1$-dimethyl-$N^2$-(4-nitro-3-trifluoromethylphenyl)-2-hexanoyloxyisobutyramidine, $N^1,N^1$-dimethyl-$N^2$-(4-nitro-3-trifluoromethylphenyl)-2-phenylacetoxyisobutyramidine.

The tangible embodiments of the compounds represented by formulae I and Ib possess the inherent applied-use characteristic of exerting an anti-androgenic response when administered within the dose range of about 0.1 mg. to about 50 mg. per kg. of body weight per day and thus are useful in treating, alleviating and/or palliation of androgen-caused and/or androgen-dependent conditions such as prostatic hyperplasia (e.g. benign prostatic hypertrophy, prostatic carcinoma), the Stein-Leventhal syndrome, idiopathic hirsutism, acne, mammary carcinoma and the like. In addition to the aforementioned applied use as therapeutic agents, the compounds of this invention (I) and (Ib) have an applied veterinary use.

In their veterinary application, the administration of these compounds is useful in reducing androgen-caused odor normally associated with the meat of male animal species, in controlling and/or eliminating the birth of normal males, and for reducing the aggressive tendencies of the male animal species; these actions of course being dependent largely by the time of administration of the anti-androgenic agent.

In those species afflicted with prostatic hypertrophy the frequency of the hypertrophic condition seems to increase with increasing age and thus represents a serious problem, even among older canine household pets. In general, hormone therapy, such as for example, administration of estrogenic substances, has not proved to be a particularly desirable treatment, not only because of the undesirable side effects due to the inherent properties of the estrogens, but also because such agents have not proved to be fully efficacious in providing meaningful remissions and cures. Surgical ablation, even though effective, is also not particularly desirable for in addition to the expected 2–3% mortality rate, many patients experience such non-fatal complications such as epididymitis, pneumonia, pyelonephritis, secondary resection, etc. Thus, the chemotherapeutic treatment of prostatic hypertrophy with concomitant absence of side effects induced by the anti-androgenic agent has been a goal long sought.

It has been determined by standard laboratory test procedures that the compounds of this invention (I) and (Ib) produce marked remissions in cases of prostatic hyperplasia without the undesirable effects elicited upon the administration of estrogens or complications inherent in any surgical procedures. Usually, depending upon the severity of the condition, a satisfactory therapeutic response is achieved in those mammal species having an adult body weight of approximately 70 kg. when 1 to 4 dosage units of the hereinafter described pharmaceutical formulations are administered to the species. Thus, a suitable dosage range for a 70 kilogram mammal is in the range of about 25 mg. to 500 mg. of the preferred active ingredients per day until symptomatic relief is obtained as ascertained by the attending diagnostician.

As stated above, the compounds of this invention (I) and (Ib) may be used as chemical castrating agents in the veterinary field.

It has been long known that male bovine and porcine species are not particularly suitable as meat producing animals. It is also known that the male animal grows at a faster rate, usually weighs more and produces a leaner carcass than does the corresponding female species. One attempt at converting the male into a more suitable commercial meat source has been by surgical castration (i.e. removal of the androgen source). However, this method has not been completely satisfactory for it involves a time-consuming process and often times leads to post-surgical problems such as infections.

Quite unexpectedly, it has been found that upon administration of a therapeutically effective quantity of the compounds of this invention (I) and (Ib) substantially the same results sought by surgical castration are obtained. Ergo these agents are referred to as chemical castrating agents. Thus, the aforementioned undesirable meat-growth characteristics are obviated and thus a more suitable animal species is available for commercial use. In addition to the enhanced growth characteristics, it is also found that these chemically castrated male animal species are devoid of the noxious odor usually associated with such animals. This noxious odor is particularly manifested by the pig species wherein the meat of the males, upon cooling, emits the well-known and quite repugnant "boar-odor" rendering the meat product unpalatable. The meat derived from the chemically castrated animal is not so tainted and indeed, it is quite palatable. This discovery is of great economic importance, in that the previously commercially unsuitable meat products were the source of a great economic waste. Although the application of this discovery is particularly suitable for the treatment of pigs, it also may be used for treating other animal species such as cattle, horses, sheep, oxen, hogs, goats and the like. Indeed, the compounds of this invention (I) and (Ib) may also be used for chemical castration for eliciting the desired effect in such avian species as drakes, geese, roosters, turkeys, and the like; such application, of course, only being during the development of the secondary sex characteristics.

In another of its veterinary uses these anti-androgens when used as chemical castrating agents have the effect of reducing the aggressive tendencies normally associated with the male animal species. This aspect is particularly useful for the treatment of valuable zoological species such as lions, tigers, elephants.

The hereinabove described chemical castration process may be affected in two manners. In mammals, the desired effect is obtained by administering a therapeutically effective quantity of the compounds of formula I or Ib to the gravid mammal shortly before and/or during the period of fetal genital formation. The results of this administration is that the litter produced will be devoid of all normal male species and will consist solely of females and "pseudo hermaphrodites", the latter having some female anatomical structures (e.g. a clitoral-like penis and a vaginal tract).

The second process for chemically castrating in animal species comprises the administration of a therapeutically effective quantity of the compounds (I) or (Ib) to a male animal species shortly before and/or during the development of its secondary sex characteristics so as to elicit an anti-androgenic effect during and after said period. The animal so treated will be suitable for use as a commercial source of meat. The other manifestations of the chemical castration are also shown in these animals.

In its process aspect then, the instant invention may be described as residing in the concept of exerting an anti-androgenic effect which comprises administering a therapeutic formulation containing as the essential ingredient, a member of the group of compounds of the general structural formula:

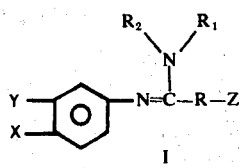

I wherein $R_1$ represents hydrogen, lower alkyl, lower cycloalkyl, hydroxy, lower alkoxy, lower cycloalkoxy, unsubstituted phenyl or phenyl substituted by nitro, trifluoromethyl or halogen, $R_2$ represents hydrogen, lower alkyl or lower cycloalkyl, or $R_1$ and $R_2$ together represent an alkylene radical having 3 to 7 carbon atoms, or the radical —$CH_2$—$CH_2$—Q—$CH_2$—$CH_2$— with Q being selected from —O—, —S—, >NH and >N-lower alkyl;

X is a member of the group consisting of nitro, trifluoromethyl, chloro, bromo and iodo, Y is a member of the group consisting of hydrogen, halogen, nitro, amino, lower alkylamino, lower dialkylamino, lower alkyl, lower alkoxy, lower alkanoyl, polyfluorolower alkoxy, polyfluorolower alkyl, polyfluorolower alkylthio,

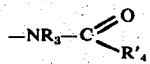

and —$NR_3SO_2R_4$ with $R_3$ being hydrogen or lower alkyl and $R_4$ being lower alkyl, aralkyl or aryl and $R'_4$ is lower alkoxy aralkoxy, aryloxy, lower alkyl, aralkyl and aryl, R is a divalent radical derived from an alkane or alkene either of which contains at least one secondary or tertiary carbon atom with the proviso that any double bond in said divalent radical derived from an alkene is not conjugated with the amidine double bond;

Z is a member of the group consisting of hydrogen, hydroxy, lower alkoxy, lower arylalkoxy, lower alkanoyloxy, lower arylalkanoyloxy, carbamoyloxy, thiocarbamoyloxy, mono- and di-lower alkyl carbamoyloxy and thiocarbamoyloxy;

and the pharmaceutically acceptable acid addition salts thereof or a member of the group of compounds of the general structural formula:

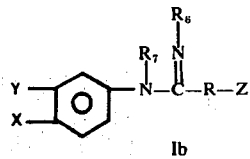

Ib wherein $R_6$ represents hydrogen, lower alkyl, lower cycloalkyl, hydroxy, lower alkoxy, lower cycloalkoxy, unsubstituted phenyl or phenyl substituted by nitro, trifluoromethyl or halogen, $R_7$ represents lower alkyl, X is a member of the group consisting of nitro, trifluoromethyl, chloro, bromo and iodo, Y is a member of the group consisting of hydrogen, halogen, nitro, amino, lower alkylamino, lower dialkylamino, lower alkyl, lower alkoxy, lower alkanoyl, polyfluorolower alkoxy, polyfluorolower alkyl, polyfluorolower alkylthio,

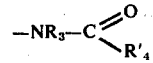

and —$NR_3SO_2R_4$ with $R_3$ being hydrogen or lower alkyl and $R_4$ being lower alkyl, aralkyl or aryl and $R'_4$ is lower alkoxy, aralkoxy, aryloxy, lower alkyl, aralkyl and aryl;

R is a divalent radical derived from an alkane or alkene either of which contains at least one secondary or tertiary carbon atom with the proviso that any double bond in said divalent radical derived from an alkene is not conjugated with the amidine double bond.

Z is a member of the group consisting of hydrogen, hydroxy, lower alkoxy, lower arylalkoxy, lower alkanoyloxy, lower arylalkanoyloxy, carbamoyloxy, thiocarbamoyloxy, mono- and di-lower alkyl carbamoyloxy and thiocarbamoyloxy;

and the pharmaceutically acceptable acid addition salts thereof.

As is true in most classes of compounds suitable for any given purposes, certain members have been found to be more desirable than others of that class. In the instant invention it is found that the more suitable compounds of formula I are those compounds wherein each of $P_1$ and $R_2$ are hydrogen or methyl and Z is hydrogen or hydroxy, and X and Y combinations for the foregoing are those wherein X is nitro, iodo, bromo or chloro with Y being trifluoromethyl or wherein X and Y are similar radicals. Specific compounds of particular interest are $N^1$, $N^1$-dimethyl-$N^2$-(4-nitro-3-trifluoromethylphenyl)-isobutyramidine, $N^1$, $N^1$-dimethyl-$N^2$-(4-chloro-3-trifluoromethyl-phenyl)isobutyramidine, $N^1$, $N^1$-dimethyl-$N^2$-(4-bromo-3-trifluoromethylphenyl) isobutyramidine, $N^1$, $N^1$-dimethyl-$N^2$-(4-iodo-3-trifluoromethylphenyl)isobutyramidine, $N^1,N^1$-dimethyl $N^2$-(3-bromo-4-nitrophenyl)isobutyramidine, $N^1,N^1$-dimethyl-$N^2$-(3-iodo-4-nitrophenyl)isobutyramidine, $N^1,N^1$-dimethyl-$N^2$-(4'-nitro-3'-trifluoromethylphenyl)-3-methyl-3-butenoamidine, $N^1,N^1$-dimethyl-$N^2$-(4'-nitro-3'-trifluoromethylphenyl)-2-hydroxyisobutyramidine, $N^1,N^1$-dimethyl-$N^2$-(4-nitro-3-trifluoromethylphenyl)isovaleroamidine, $N^1,N^1$-dimethyl-$N^2$-(4'-nitro-3'-trifluoromethylphenyl)-2,3-dimethylbutyramidine, $N^1$-methyl-$N^2$-(3-trifluoromethyl-4-nitrophenyl)isobutyramidine.

In its subgeneric concepts the instant invention relates to the application of the compounds of this invention (I) and (Ib) to mammals for the treatment of benign prostatic hypertrophy, acne, hirsutism, mammary carcinoma, prostatic carcinoma and other androgen dependent body malfunctions and to their use in the aforementioned veterinary application.

The active substituted amidines (I) and (Ib) of this invention can be administered orally in the form of tablets, capsules, elixirs, and the like or may be administered by parenteral injection. In tablet form they are compounded with an inert pharmaceutical carrier which may contain a suitable binder such as, for example, gums, starches, and sugars. They may also be incorporated into gelatin capsules or formulated into elixirs which have the advantage of being susceptible to manipulations in flavor by the addition of standard natural or synthetic flavoring agents. Highly satisfactory administration may also be achieved in the form of aqueous parenteral suspension. The compounds of this invention effectively elicit an antiandrogenic effect at about 1 to about 50 mg./kg. of body weight on a daily basis. Preferably, these formulations are so proportioned as to afford a unit dosage of from about 1 to about 100 mg. of active amidine. Particularly preferred are unit dosages ranging from about 5 to about 25 mg. Preferably, the compounds are administered orally.

Furthermore, the therapeutically active ingredient may be admixed with the food of the species to which the administration is desired, thereby obtaining a therapeutically efficacious dose level.

Representative embodiments of the formulations conntaining the compositions of this invention are as follows:

TABLET FORMULATIONS

| Formula A (5 mg.) | Milligrams per Tablet |
|---|---|
| $N^1, N^1$—dimethyl—$N^2$—(3-trifluoromethyl-4-nitrophenyl) isobutyramidine | 5.0 |
| Starch, Food Grade | 5.0 |
| Lactose, U.S.P. (Spray Dried) | 89.5 |
| Magnesium Stearate, U.S.P. | 0.5 |
|  | 100.0 |

| Formula B (25 mg.) |  |
|---|---|
| $N^1, N^1$—dimethyl—$N^2$—(3-trifluoromethyl-4-nitrophenyl)-isobutyramidine | 25.0 |
| Starch, Food Grade | 10.0 |
| Lactose, U.S.P. (Spray Dried) | 164.0 |
| Magnesium Stearate, U.S.P. | 1.0 |
|  | 200.0 |

Pass the $N^1,N^1$-dimethyl-$N^2$-(3-trifluoromethyl-4-nitrophenyl)-isobutyramidine through a high speed mill equipped with a 100 to 150 mesh screen. Blend the milled $N^1,N^1$-dimethyl-$N^2$-(3-trifluoromethyl-4-nitrophenyl)-isobutyramidine with the starch in a suitable mixing vessel. Add an equal weight of the spray dried lactose to the blend and mix until uniform. Combine the resultant blend with the remainder of the spray dried lactose and mix until uniform. Charge the magnesium sterate with a portion of the active tablet mix and blend. Blend the magnesium stearate mix with the remaining active tablet base. Continue mixing until uniform. Compress to target weight (100.0 mg. for 5 mg. tablet and 200.0 mg. for 25 mg. tablet).

CAPSULE FORMULATIONS

| Formula | Milligrams per Capsule |
|---|---|
| $N^1, N^1$—dimethyl—$N^2$—(3-trifluoromethyl-4-nitrophenyl)-isobutyramidine | 5.0 |
| Lactose, U.S.P. (Spray Dried) | 292.0 |
| Magnesium Stearate, U.S.P. | 3.0 |
|  | 300.0 |

Blend ingredients until uniformly mixed. Fill into hard gelatin capsule.

PARENTERAL SUSPENSION

| Formula A (5 mg.) | Milligrams per Milliliter |
|---|---|
| $N^1, N^1$—dimethyl—$N^2$—(3-trifluoromethyl-4-nitrophenyl)-isobutyramidine | 5.00 |
| Methyl Cellulose 15 cps. U.S.P. | 0.05 |
| Sodium Citrate, Dihydrate | 6.00 |
| Benzyl Alcohol, NF | 9.00 |
| Methylparaben, U.S.P. | 1.80 |
| Propylparaben, U.S.P. | 0.20 |
| Water for Injection, U.S.P. | 1.00 |
| Formula B (25 mg.) |  |
| $N^1, N^1$—dimethyl—$N^2$—(3-trifluoromethyl-4-nitrophenyl)-isobutyramidine | 25.00 |
| Methyl Cellulose 15 cps. U.S.P. | 0.25 |
| Sodium Citrate, Dihydrate | 30.00 |
| Benzyl Alcohol, NF | 9.00 |
| Methylparaben, U.S.P. | 1.80 |
| Propylparaben, U.S.P. | 0.20 |
| Water for Injection, U.S.P. q.s. a.d. | 1.00 |

Charge 45 liters of water for injection into a suitable stainless steel vessel and heat to 85°–90°C. With vigorous agitation, slowly sprinkle the methyl cellulose into the hot water (5 mg. for formula A or 25 for formula B). Agitate until the methyl cellulose is thoroughly dispersed and wetted. Add approximately, 30 liters of cold (0°–5°C) water for injection. Cool the entire mixture to 8°C. Dissolve the sodium citrate (600 gm. of formula A or 3000 gm. for formula B) in enough water for injection to make 5 liters of solution. Slowly and with agitation add this solution to the cooled cellulose solution. Dissolve the parabens (180 gm. of methyl and 20 gm. of propyl) in 900 gm. of benzyl alcohol which has been heated to 30°C. Charge this solution to the chilled methyl cellulose solution. Bring the resulting solution to 90 liters with water for injection and agitate until uniform. In a sterile area, pass the batch through a sterile filter. Aseptically transfer about 3.5 liters of the sterile methyl cellulose solution to a separate container reserving the remainder of the batch in a sterile stainless steel mixing tank. Slurry the $N^1,N^1$-dimethyl-$N^2$-(3-trifluoromethyl-4-nitrophenyl)-isobutyramidine in sterile colloid mill with about 2 liters of the separated methyl cellulose solution and add the slurry to the solution in the mixing tank. Rinse the slurry container and the mill with the remaining 1.5 liters of reserved methyl cellulose solution and add the rinse to the mixing tank. Rinse the slurry container and mill with 2 liters of water for injection and add the rinse to the mixing tank. Adjust the volume in the mixing tank to 100 liters with water for injection and agitate until uniform. The batch affords 100 liters of sterile suspension having the proportions of formula A or formula B.

I claim:
1. Compounds of the general formula

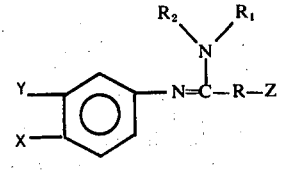

wherein $R_1$ represents hydrogen, lower alkyl, lower cycloalkyl, hydroxy, lower alkoxy, lower cycloalkoxy, unsubstituted phenyl or phenyl substituted by nitro, trifluoromethyl or halogen, $R_2$ represents hydrogen, lower alkyl or lower cycloalkyl, X is a member of the group consisting of nitro, trifluoromethyl, chloro, bromo and iodo, Y is a member of the group consisting of hydrogen, halogen, nitro, amino, lower alkylamino, lower dialkylamino, lower alkyl, lower alkoxy, lower alkanoyl, polyfluorolower alkoxy, polyfluorolower alkyl, polyfluorolower alkylthio,

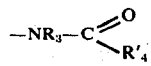

and —NR$_3$SO$_2$R$_4$ with R$_3$ being hydrogen or lower alkyl, R$_4$ being lower alkyl, and R$'_4$ is lower alkoxy and lower alkyl.

R is a divalent radical derived from an alkane or alkene having up to eight carbon atoms, either of which contains at least one secondary or tertiary carbon atom with the proviso that any double bond in said divalent radical derived from an alkene is not conjugated with the amidine double bond;

Z is a member of the group consisting of hydroxy, lower alkoxy, and the pharmaceutically acceptable acid addition salts thereof.

2. Compounds of claim 1 wherein Z is hydroxy.

3. Compounds of claim 2 wherein R$_1$ and R$_2$ are lower alkyl.

4. Compounds of claim 1 wherein X is nitro, and Y is trifluoromethyl.

5. Compounds of claim 2 wherein X is nitro, and Y is trifluoromethyl.

6. Compounds of claim 2 wherein X is nitro, and Y is bromo.

7. Compounds of claim 2 wherein X is nitro, and Y is chloro.

8. Compounds of claim 2 wherein X is chloro, and Y is trifluoromethyl.

9. Compounds of claim 2 wherein X is bromo, and Y is trifluoromethyl.

10. Compounds of claim 2 wherein X is iodo, and Y is trifluoromethyl.

11. Compounds of claim 5 wherein R$_1$ and R$_2$ are methyl.

12. A compound of claim 2, said compound being N$^1$,N$^1$-dimethyl-N$^2$-(3'-trifluoromethyl-4'-nitrophenyl)-2-hydroxyisobutyramidine.

* * * * *